(12) United States Patent
Allinson et al.

(10) Patent No.: US 8,078,317 B2
(45) Date of Patent: Dec. 13, 2011

(54) DISPENSING OF RESTRICTED GOODS

(75) Inventors: John Clive Allinson, Balwyn North (AU); Garry David Boyd, Williamstown (AU)

(73) Assignee: Bluepoint International Pty Ltd. (AU)

( * ) Notice: Subject to any disclaimer, the term of this patent is extended or adjusted under 35 U.S.C. 154(b) by 442 days.

(21) Appl. No.: 12/089,461

(22) PCT Filed: Oct. 6, 2006

(86) PCT No.: PCT/AU2006/001458
§ 371 (c)(1),
(2), (4) Date: Apr. 7, 2008

(87) PCT Pub. No.: WO2007/041767
PCT Pub. Date: Apr. 19, 2007

(65) Prior Publication Data
US 2008/0262649 A1 Oct. 23, 2008

(30) Foreign Application Priority Data
Oct. 7, 2005 (AU) ................................ 2005905515

(51) Int. Cl.
*G06F 17/00* (2006.01)
(52) U.S. Cl. ........ 700/237; 700/236; 700/240; 700/242; 700/244
(58) Field of Classification Search .................. 700/232, 700/237, 240, 241, 244
See application file for complete search history.

(56) References Cited

U.S. PATENT DOCUMENTS

| 4,845,636 | A | 7/1989 | Walker | |
|---|---|---|---|---|
| 6,529,801 | B1 * | 3/2003 | Rosenblum | 700/237 |
| 6,711,460 | B1 * | 3/2004 | Reese | 700/244 |
| 6,735,497 | B2 * | 5/2004 | Wallace et al. | 700/237 |
| 6,766,218 | B2 | 7/2004 | Rosenblum | |
| 6,892,941 | B2 | 5/2005 | Rosenblum | |
| 7,006,893 | B2 | 2/2006 | Hart et al. | |
| 7,080,755 | B2 | 7/2006 | Handfield et al. | |

(Continued)

FOREIGN PATENT DOCUMENTS
AU 2003203618 1/2004
(Continued)

*Primary Examiner* — Timothy Waggoner
(74) *Attorney, Agent, or Firm* — Connolly Bove Lodge & Hutz LLP

(57) ABSTRACT

A dispenser for dispensing restricted goods such as pharmaceuticals by an pharmacist to a purchaser with a prescription includes a cabinet containing an inventory storage system, a purchaser transaction module, a reject system and a control system. The inventory storage system includes product storage in rows and columns. The purchaser transaction module including an audio communication link from the dispenser to the pharmacist, a payment transaction system in the dispenser to verify payment for the product and an issue tray in the dispenser that is locked until the pharmacist releases the product to the purchaser. The reject system securely removes product to a reject hopper at any time after the product is held by the product selection device but prior to the pharmacist releasing the product from the issue tray. The control system includes means to enable the pharmacist to view the prescription and the purchaser. The control unit includes a product identification system that identifies and stores the location of each product by its row and column and cooperates with a product selection device that verifies that the product selected is correct and holds and carries the product from its storage location to one or more of a printing location, viewing location and issue tray all located within the dispenser. The pharmacist is able to actuate the reject system or unlock the issue tray.

10 Claims, 15 Drawing Sheets

U.S. PATENT DOCUMENTS

| | | | |
|---|---|---|---|
| 7,123,989 B2 * | 10/2006 | Pinney et al. | 700/237 |
| 7,151,982 B2 | 12/2006 | Liff et al. | |
| 7,344,047 B2 * | 3/2008 | Gilmore | 221/2 |
| 7,721,914 B2 | 5/2010 | Handfield et al. | |
| 7,735,681 B2 | 6/2010 | Handfeld et al. | |
| 7,774,097 B2 | 8/2010 | Rosenblum | |
| 7,783,378 B2 | 8/2010 | Pinney et al. | |
| 7,783,379 B2 | 8/2010 | Beane et al. | |
| 7,787,986 B2 | 8/2010 | Pinney et al. | |
| 2005/0023286 A1 | 2/2005 | Pinney et al. | |

FOREIGN PATENT DOCUMENTS

| | | |
|---|---|---|
| AU | 2004101011 | 1/2005 |
| WO | 2006070359 A2 | 7/2006 |

* cited by examiner

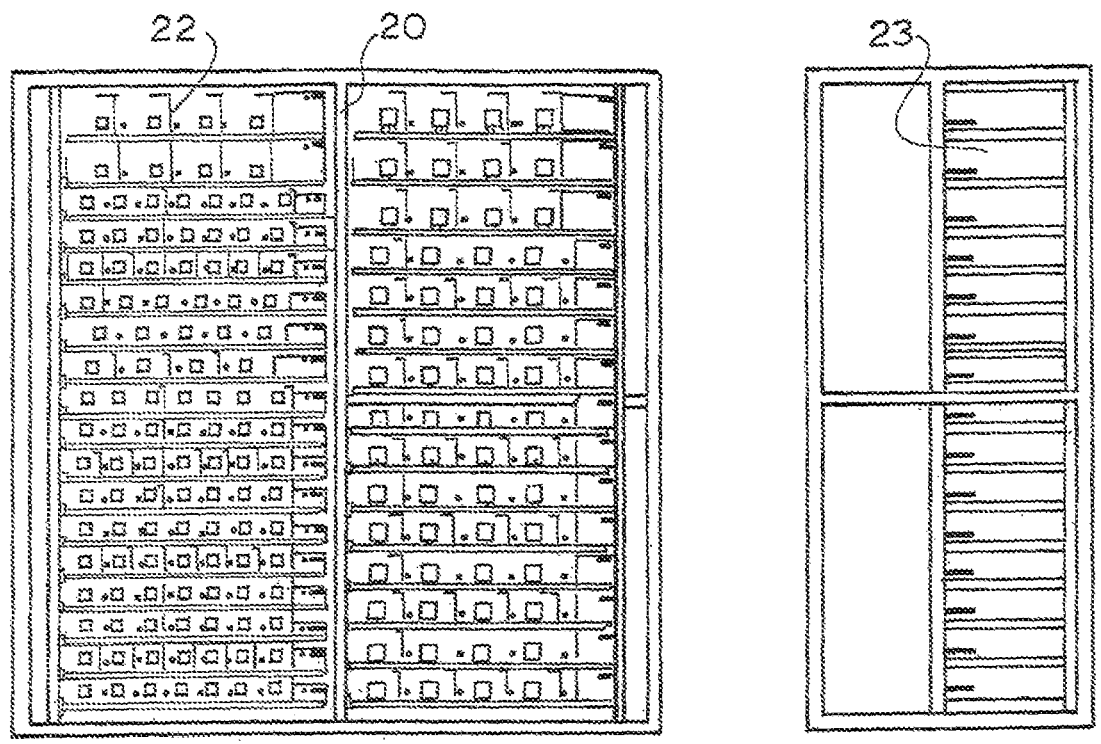
Fig. 5.
Fig. 6.
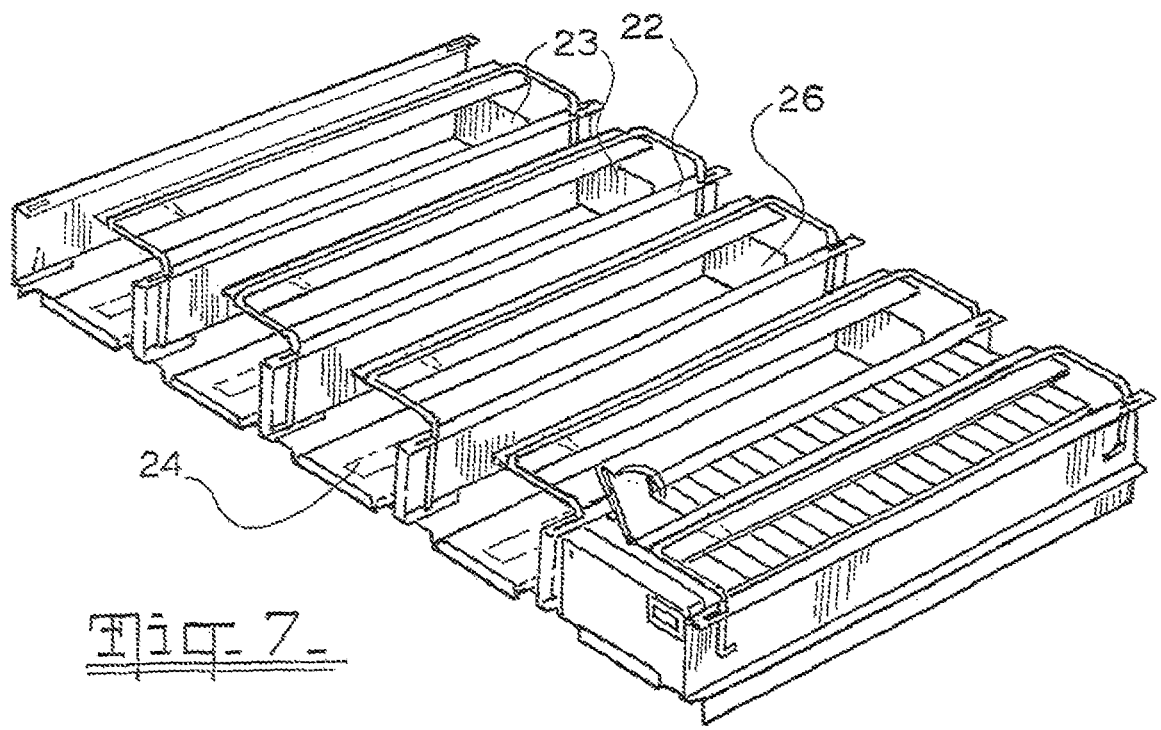
Fig. 7.

DISPENSING OF RESTRICTED GOODS

CROSS REFERENCE TO RELATED APPLICATIONS

This application is a National Phase filing under 35 U.S.C. §371 of PCT/AU2006/001548 filed Oct. 6, 2006, which claims priority to Patent Application No. 2005905515, filed in Australia on Oct. 7, 2005. The entire contents of each of the above-applications are incorporated herein by reference.

This invention relates to the vending and dispensing of goods that have government regulations controlling the their sale and in particular is concerned with dispensing ethical pharmaceuticals that normally require a prescription from a physician.

BACKGROUND TO THE INVENTION

The problem of providing remote and after hours supply of pharmaceuticals has been addressed before.

U.S. Pat. Nos. 6,330,491 and 8,438,451 disclose a system for automating the dispensing of drugs using a dispensing machine. The script is sent over the internet from the doctors premises or the patient's premises and the drugs are made available at the dispensing machine by the pharmacist. No direct contact between the patient and the pharmacist occurs.

U.S. Pat. Nos. 6,584,121 and 6,735,497 provide an internet based system of communicating a script to a pharmacy which then makes the drugs available by mall or at a designated pick up point which may be a dispensing machine. Again there is no contact between the patient and pharmacist.

U.S. Pat. No. 6,871,733 discloses a pharmacy remote link for scanning and sending script to Pharmacy and also for payment. There is no disclosure of a dispensing machine.

U.S. Pat. Nos. 8,529,801 and 6,786,218 disclose a similar arrangement in that a script is sent by a doctor to a pharmacist for delivery from a vending machine. The vending machine includes a gantry row and column product transport system with magazines of product and uses a pusher to move product from each product magazine onto the gantry carrier. The gantry carrier has a bar code scanner to identify the contents of each magazine. The machine includes a reject bin if the bar code scan is not positive. The dispenser needs an authorization code to actuate the dispensing of the drugs.

These prior art attempts at dealing with this problem depend on the doctor or patient sending the prescription electronically to the pharmacist whereas often the patient has a hard copy of the prescription and may not be able to send this to the pharmacist. The dispensing machines do not allow any interaction by the consumer with the pharmacist and this is usually unsatisfactory for the consumer and in some jurisdictions does not comply with the regulations.

Australian patent application 2003203618 discloses a pharmaceutical dispenser communicating with a remote pharmacist. The dispenser has a video that can scan one of prescription or purchaser and incorporates a printer to print a label.

The dispenser can be actuated by the pharmacist to release the package.

This disclosure goes part of the way in improving the control and quality of remote dispensing.

It is an object of this invention to provide a remoter dispensing machine for pharmaceuticals or other restricted goods that allows for direct communication between the purchaser and the vendor in a manner that is convenient and safe.

BRIEF DESCRIPTION OF THE INVENTION

To this end the present invention provides a method of dispensing restricted products from an authorized vendor to an approved purchaser which includes the steps of
a) providing a dispenser containing an inventory of restricted goods
b) providing an audio communication and optionally a data link from the dispenser to the authorized vendor
c) providing means in the dispenser to enable the vendor to verify the purchaser's status as an approved purchaser
d) providing an inventory system that includes product storage in rows and columns and a product identification system that identifies the location of each product by its row and column
e) providing a product selection device that verifies that the product selected is correct and holds and carries the product from its storage location to one or more of a printing location, viewing location and issue tray all located within the dispenser
f) optionally providing a printing location to enable the product to be labeled
g) providing visual viewing means for the vendor to view the product before it is placed in the issue tray
h) providing a payment transaction system in the dispenser to verify payment for the product
i) providing an issue tray in the dispenser that is locked until the vendor releases the product to the purchaser
j) the dispenser including a reject system that securely removes product to a reject hopper at any time after the product is held by the product selection device but prior to the vendor releasing the product from the issue tray.

This method overcomes the short comings of the prior art by providing, in the dispenser at least an audio link to enable the vendor and the purchaser to ask questions and ensure that each party to the transaction is satisfied and ensure compliance with the safety aspirations of the regulations. The vendor is additionally able to view and verify that the product is as specified and is able to abort the transaction if required.

The method may also include the steps of
a) providing a connection to a management sewer
b) providing a means in management server for identifying approved vendors
c) providing a means to manage authorised users, user locations, dispensing terminals, and the relationship between authorised vendors and dispensing terminals Throughout this specification the following terms have the meanings as set out below:

Restricted goods: means goods that require a licensed vendor and an authorization or licence to purchase or proof of age and includes pharmaceuticals, medical products, alcohol, cigarettes and firearms.

Authorised vendor: means a person licensed or approved to sell restricted goods and includes pharmacists, doctors, health professionals, holders of liquor licenses, managers of gambling and wagering establishments and firearms and explosives dealers and persons who can carry out some of these tasks on behalf of the licensed person.

Authorized purchaser: means anyone who can pass the age qualification or possess an authorisation to purchase such as a physician's prescription or a gun licence.

Payment transaction system; means any means to conclude the exchange of goods for consideration and includes a cash receiving system, electronic funds transfer, credit card transaction system, account debiting system, or any voucher or government agency authority such as the dispensing of pharmaceuticals to authorized persons free of charge.

The method is able to cope with several vendors and several dispensing machines. For example a pharmaceutical retailer may employ several registered pharmacists and have several dispensing machines at different locations. Any one of the pharmacists can respond to purchaser requests at any of the dispensers according to need.

The dispenser may be any secure device that can hold product and enable the purchaser to transact the purchase and collect the product.

In another aspect the present invention provides a dispenser for dispensing restricted goods by an authorized vendor to an approved purchaser which includes:

a) A cabinet containing an inventory storage system, a purchaser-transaction module, a reject system and a control system
b) Said inventory storage system includes product storage in rows and columns
c) Said purchaser transaction module including an audio communication link from the dispenser to the authorized vendor, a payment transaction system in the dispenser to verify payment for the product and an issue tray in the dispenser that is locked until the vendor releases the product to the purchaser
d) Said reject system securely removes product to a reject hopper at any time after the product is held by the product selection device but prior to the vendor releasing the product from the issue tray.
e) Said control system including
  i) means to enable the vendor to verify the purchasers status as an approved purchaser
  ii) a product identification system that stores the location of each product by its row and column
  iii) a product selection device that verifies that the product selected is correct and holds and carries the product from its storage location to one or more of a printing location, viewing location and issue tray all located within the dispenser
  iv) an optional printer to enable the product to be labeled
  v) an optional visual viewing means for the vendor to view the product before it is placed in the issue tray
  vi) actuation means to enable the vendor to actuate the reject system or unlock the issue tray.

The cabinet is intended to be a secure device akin to a financial automatic teller machine but in other respects similar to a product vending machine although the products are unlikely to be displayed to the purchaser until the transaction is completed.

Any suitable inventory storage system that uses a row and column system is suitable for this invention. Each row may consist of a shelf with a multiple set of compartments corresponding to the columns. Preferably the compartment widths are variable to accommodate various sizes of package and containers including packets and bottles. Thus each shelf may contain a different number of compartments (columns). The shelf spacing may also be varied so that ail shelves are not necessarily equidistant. The arrangement of the compartment and shelf spacing is able to be identified by the controller or programmed in the controller so that the location of each storage location and product can be identified in the row and column configuration. The controller can recognize the position of each horizontal row and vertical column and also identify each product placed in each location. Identification is matched to a data base and confirmation that the correct product is in the correct chute location, if not the controller can pick and reject the product or follow a configurable command, to block picking from this location. The purchaser transaction module may include input devices such as a keyboard, keypad and an audio link to a registered vendor. This enables the vendor and purchaser to converse and clarify any issues relating to the purchase and the use of the purchased product. In certain facilities the registered vendor would be able to access the transaction module and process the supply of a product on behalf of the purchaser.

Preferably, the module will also include a video camera to enable the vendor to view the purchaser and capture an image of the purchaser and the purchaser's identification document such as driver's licence which may establish identity and age as prerequisites for some transactions. The purchaser transaction module also preferably includes a scanner to scan any authorization documents such as a prescription from a physician or a gun licence. It is within the scope of this invention that the authorization documents may have previously been forwarded to the vendor or be available for viewing on a network accessible database in which case the purchaser need only establish that they are the person to whom the authorization relates either by identification or use of an identification code or password. In some countries this is referred to as an electronic prescription. An essential component of the purchaser transaction module is the payment transaction system which may provide for the insertion of a credit or debit card and a personal identification number (PIN) and password or some other appropriate identification that enables the cost of the transaction to be debited against the account of the person or government agency responsible. The payment transaction may be completed after initiation of the transaction or at any time before the product is released from the collection or issue tray.

Based on the type of facility the payment module may not be necessary. Payment can be completed within existing processes in the dispensary point of sale. The system can output a coupon to record payment by other method if required. The collection tray is a compartment in the dispenser into which the goods to be dispensed are transferred by the product selection system. It incorporates a lock that makes it inaccessible until the vendor actuates release. The collection tray also includes a reject mechanism that enables the issue tray to be emptied into a reject bin or for the products to be removed and placed in the reject receptacle should the transaction be aborted before the vendor actuates the release.

The reject system when actuated controls the product selection device so that it holds and carries the product to the reject receptacle. If the product selection device has already delivered the product to the collection tray when the reject system is actuated. It controls the collection tray to prevent it being unlocked until the products in the collection tray are removed to the reject bin. It is within the scope of this invention to incorporate two reject bins one located in the processing module, and the second one located below the collection tray The control system is primarily a programmable computer with a data storage system that is primarily accessed by the vendor but is initiated by the purchaser beginning a transaction. The purchaser can only begin a transaction request if an authorised vendor is logged into the system and available for service. Once the product request is made the control system is programmed to search the inventory database to check if it is available. The product request may be made by the presentation of the purchase authorisation such as a pharmaceutical prescription or by the vendor or purchaser keying in the product code or the purchaser verbally requesting the product and the vendor keying in the code. Once the product has been identified end its availability and location in the storage identified, the product selection system can be actuated. The product selection system is preferably a pick and place gantry system moving horizontally and vertically in accordance with the compartment and shelf locations of the storage system. The pick up unit incorporates a bar code reader or similar device to verify that the bar code on the product in the compartment is the same as the bar code of the requested product, if it is incorrect the unit picks up the product and conveys it directly to a chute that leads to the reject bin, if it is correct the pick up unit carries it to the label printing station. The pick up unit can use any pick and hold mechanism such as a suction grip for light packages or a robotic hand. The printing station is intended primarily for use with pharmaceuticals where it is conventional for the pharmacist to add a label specifying the quantity and timing of the administration of the pharmaceutical. It may also indicate the date the product was dispensed from the dispenser. The product selection device may then convey the product to a video camera location so that the vendor and optionally the purchaser can view the product to ensure it is correct, if at this point the vendor decides the product is incorrect or incorrectly labeled the transaction may be aborted and the product selection unit picks up the product and conveys it directly to a chute that leads to the reject bin. If the vendor approves the product it is conveyed to the issue tray. When the payment transaction is completed the vendor actuates the unlocking of the issue tray so that the product can be collected by the purchaser. Any documentation, such as a receipt or a repeat prescription or authorization for another purchase, is preferably deposited in the issue tray although they could be issued through another slot in the purchaser module.

DETAILED DESCRIPTION OF THE INVENTION

A preferred embodiment of the invention which is a pharmaceutical retelling system and dispenser for pharmaceutical products will ha described with reference to the drawings in which:

FIG. 1 provides a schematic representation of the pharmacy network system with a terminal remote dispensing machine (RDM);

FIG. 5 is a detailed view of a possible shelf layout of the storage unit of the RDM;

FIG. 6 is an end cross section of FIG. 5;

FIG. 7 is a detail of the tray construction for each shelf of the RDM;

Figure 8:
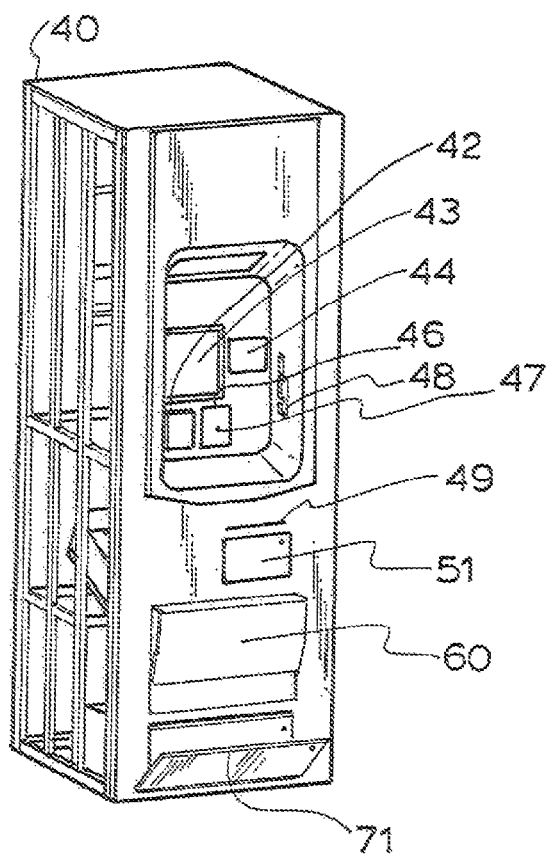
FIG. 8 is an external view of the purchaser interface module of the RDM.
Figure 11A:
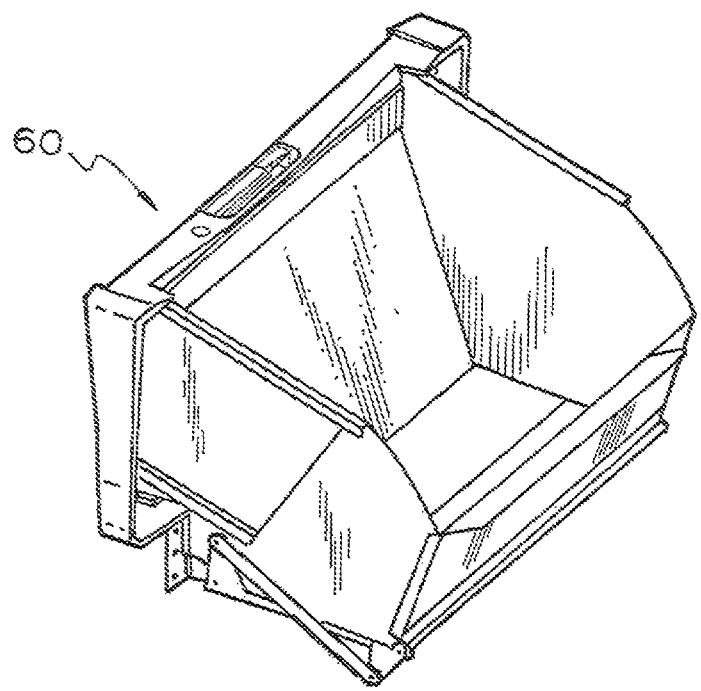
Figure 11B:
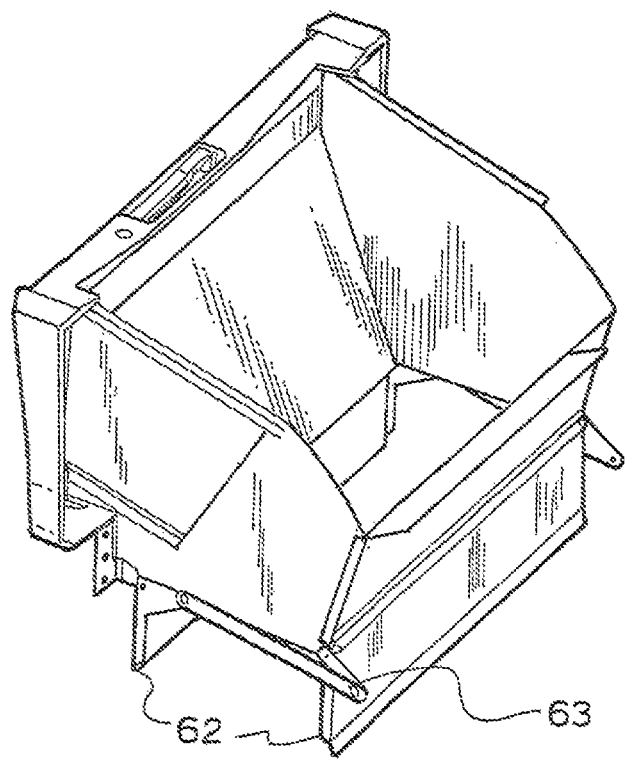
Figure 12A:
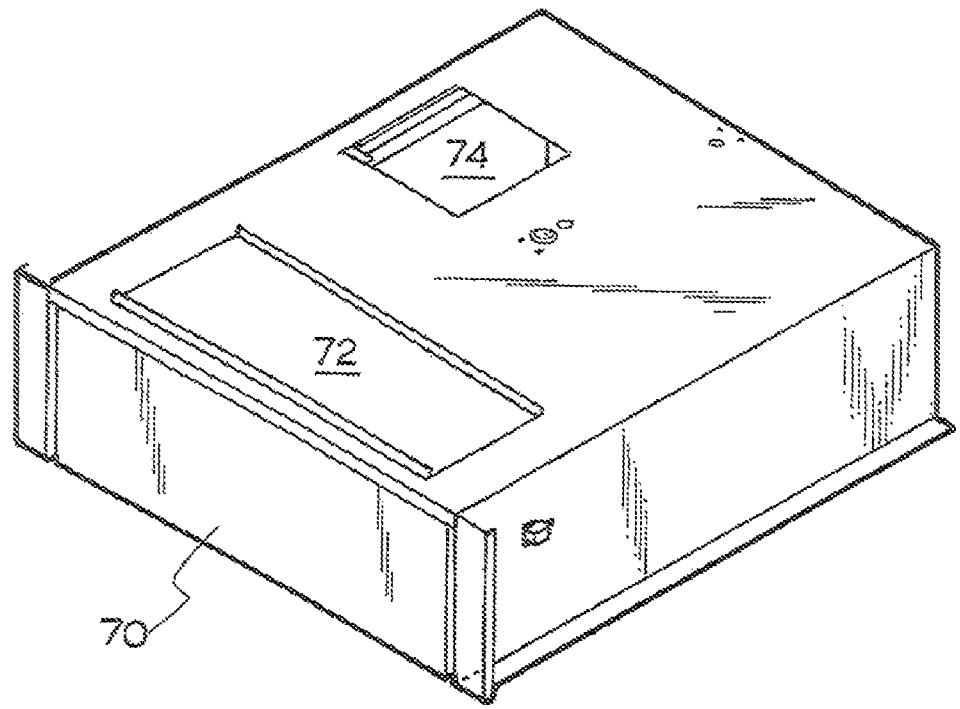
Figure 13A:
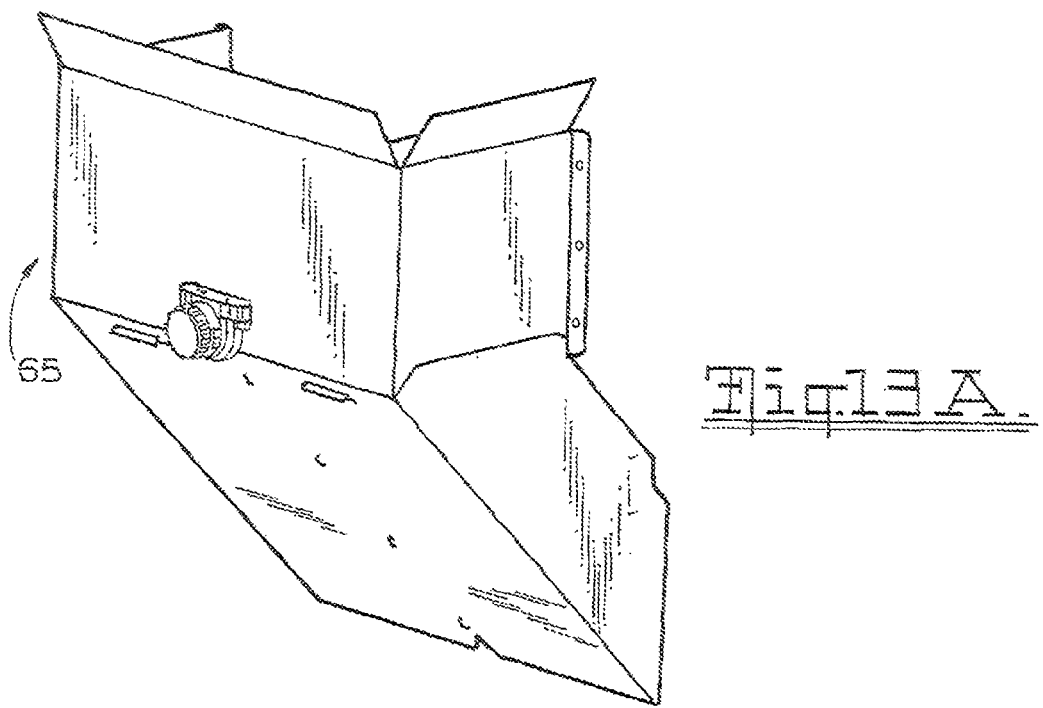
Figure 14:
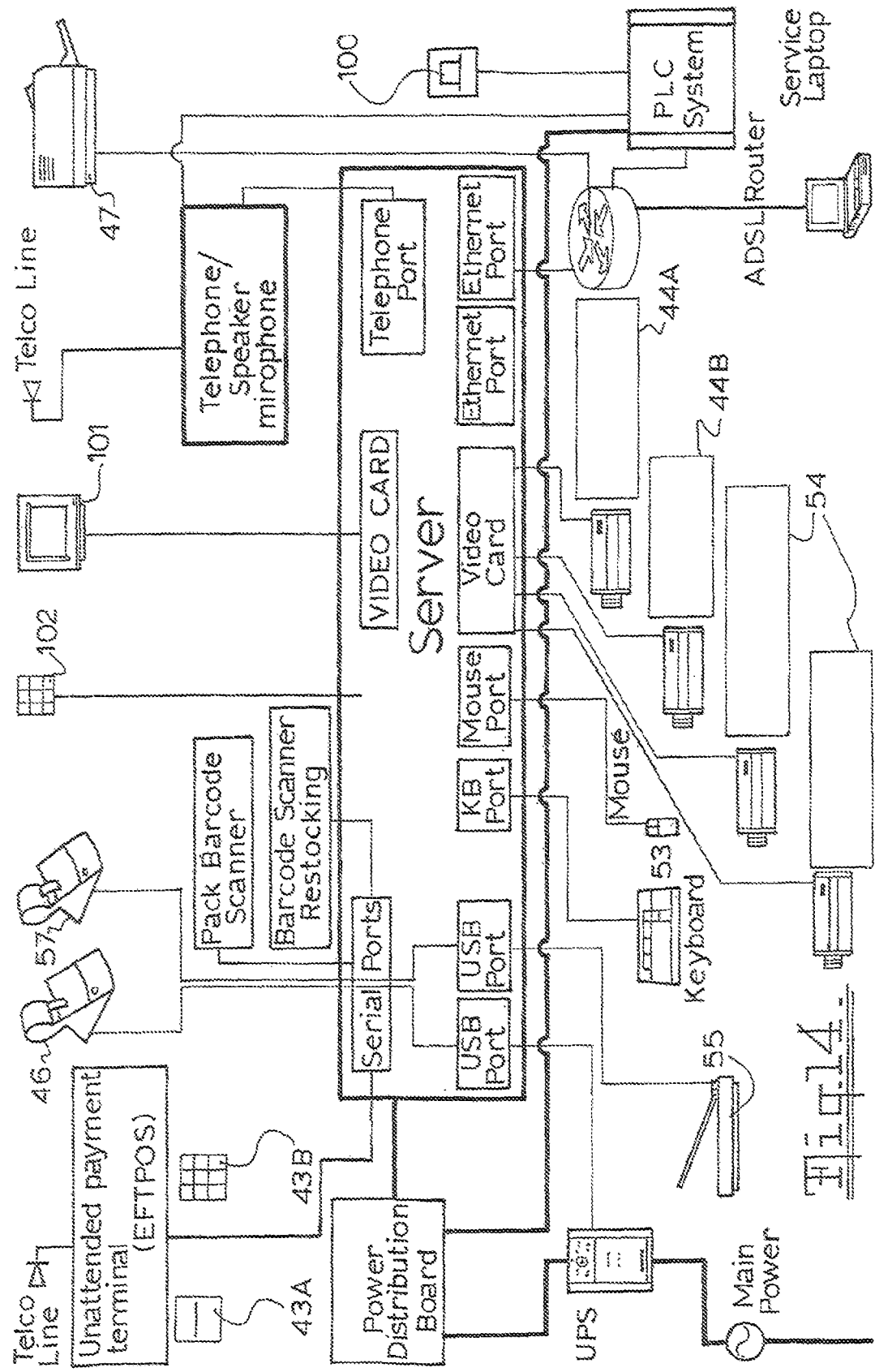
Figure 15:
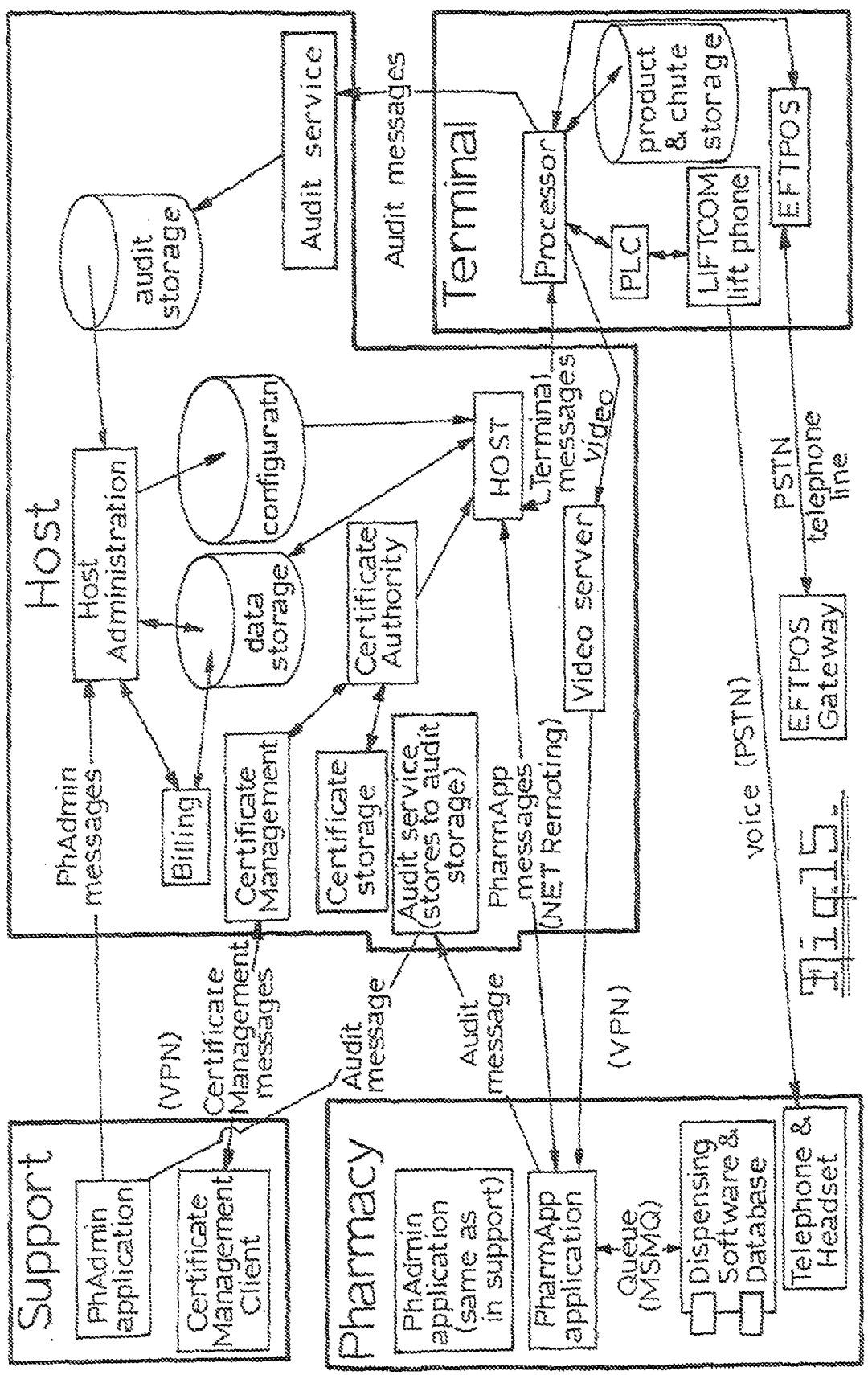
Figure 15:
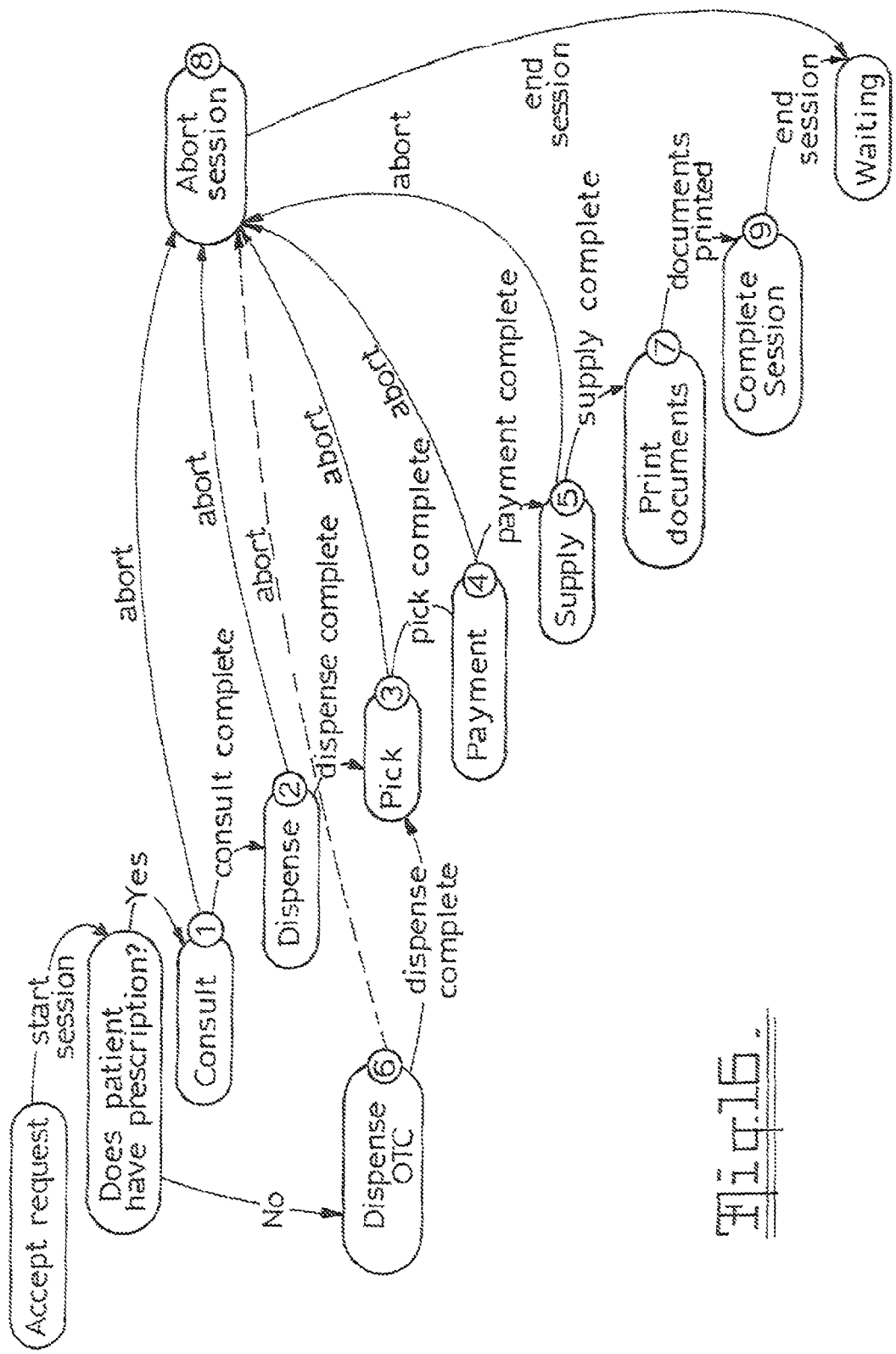
Figure 17:
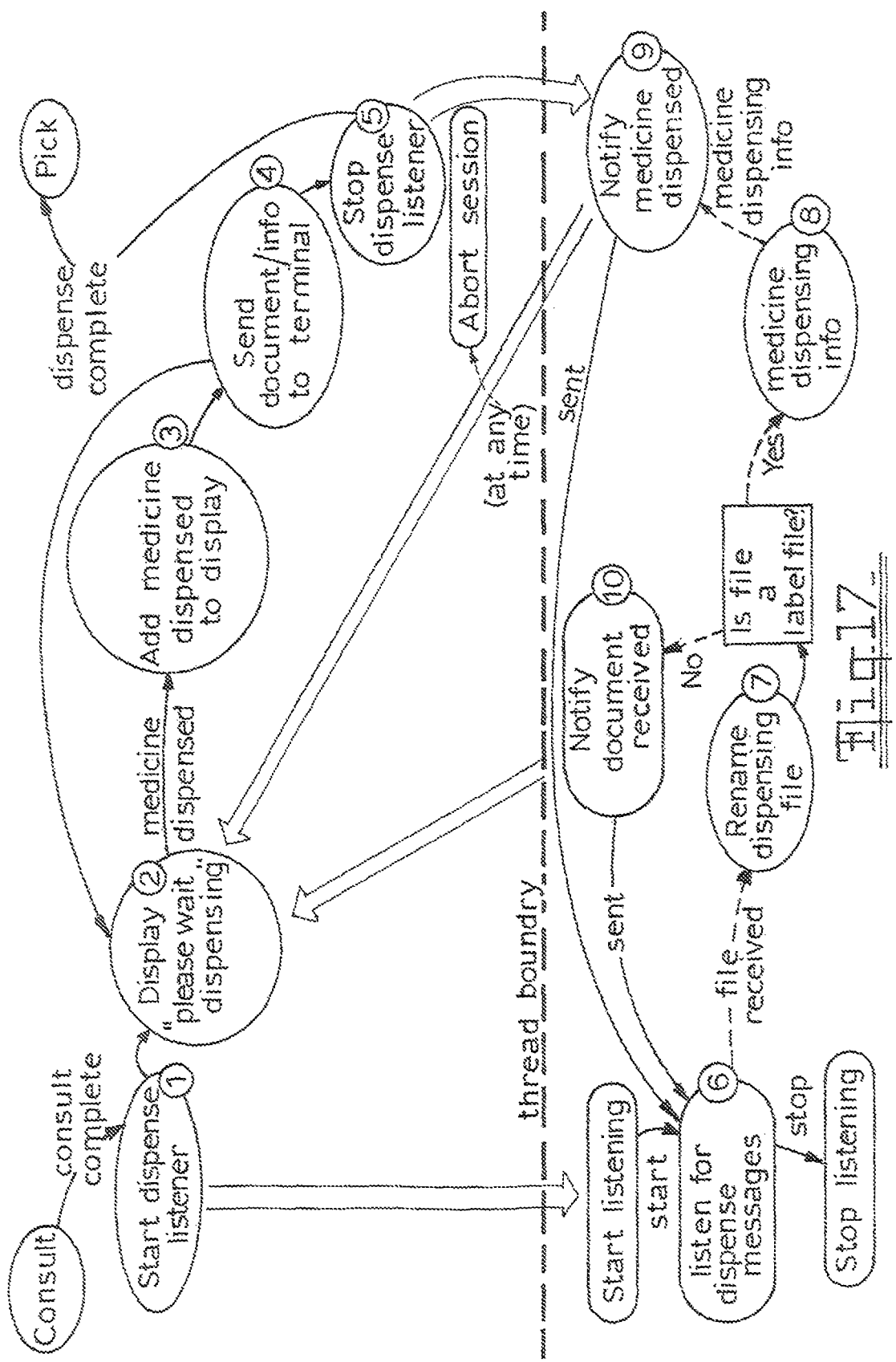
Figure 18:
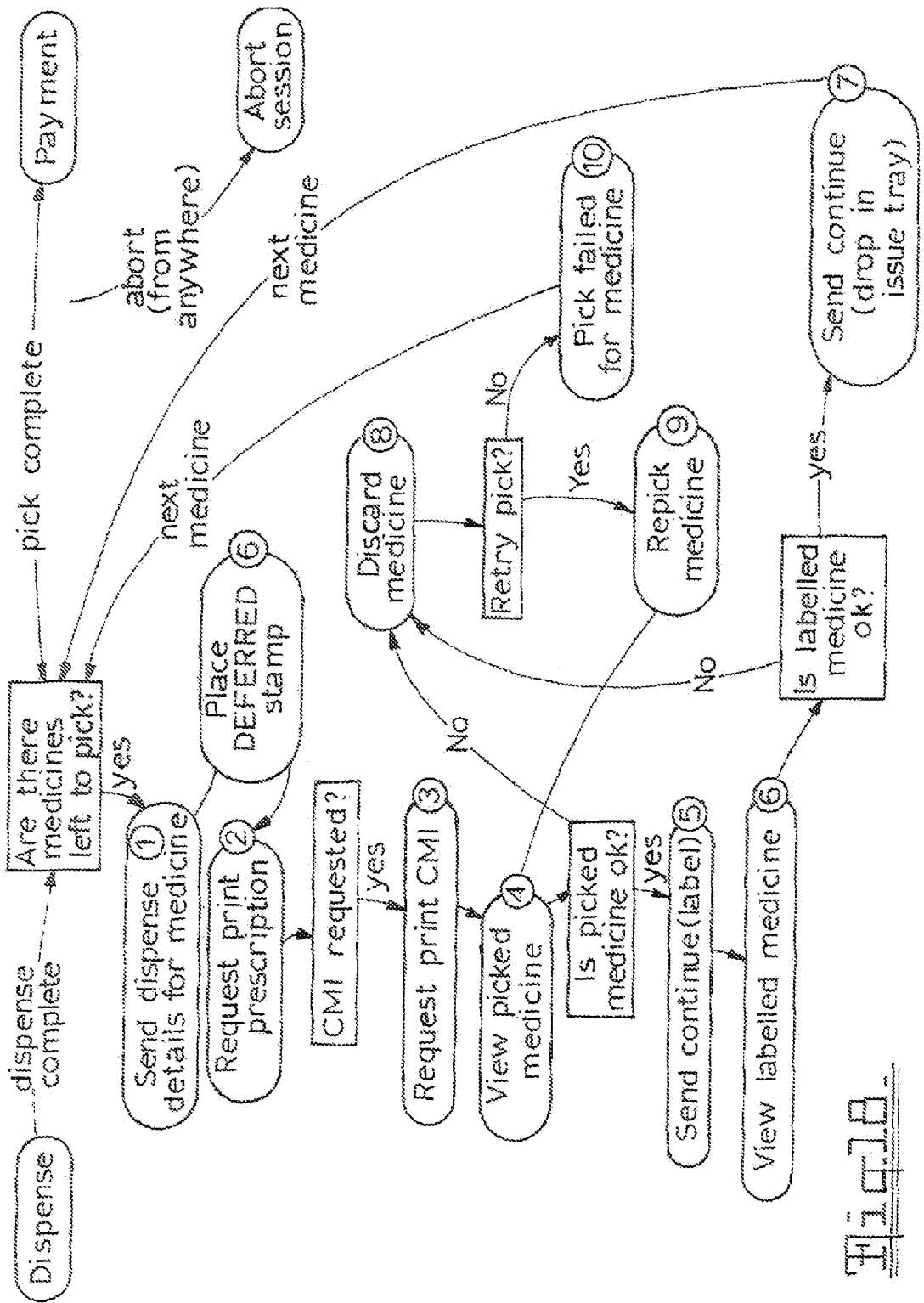

FIGS. 11A and B illustrate the issue tray of the module of FIG. 8;

FIGS. 12A and B illustrate the reject bin of the module of FIG. 8;

FIGS. 13A and B illustrate the product chute of the module of FIG. 8;

FIG. 14 schematically illustrates the hardware components used in the purchaser interface module of the RDM;

FIG. 15 is a schematic diagram of the process overview of the pharmacy dispensing system;

FIG. 16 is a flowchart setting out the script handling process for this preferred pharmacy embodiment;

FIG. 17 is a flow chart illustrating the first phase of the supply of goods sequence;

FIG. 18 is a flow chart illustrating the second phase of the supply of goods sequence.

Figure 1:
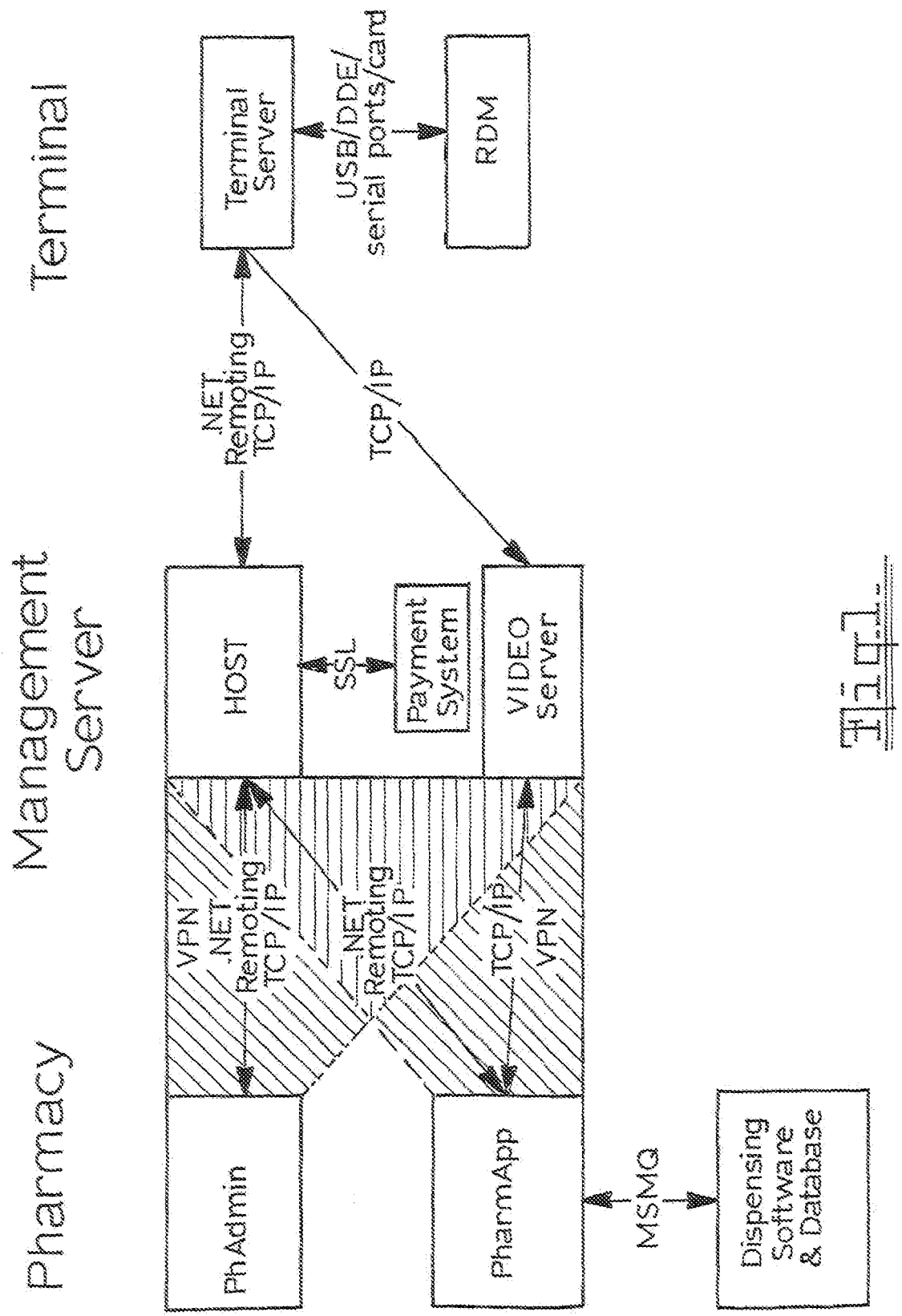
Figure 2:
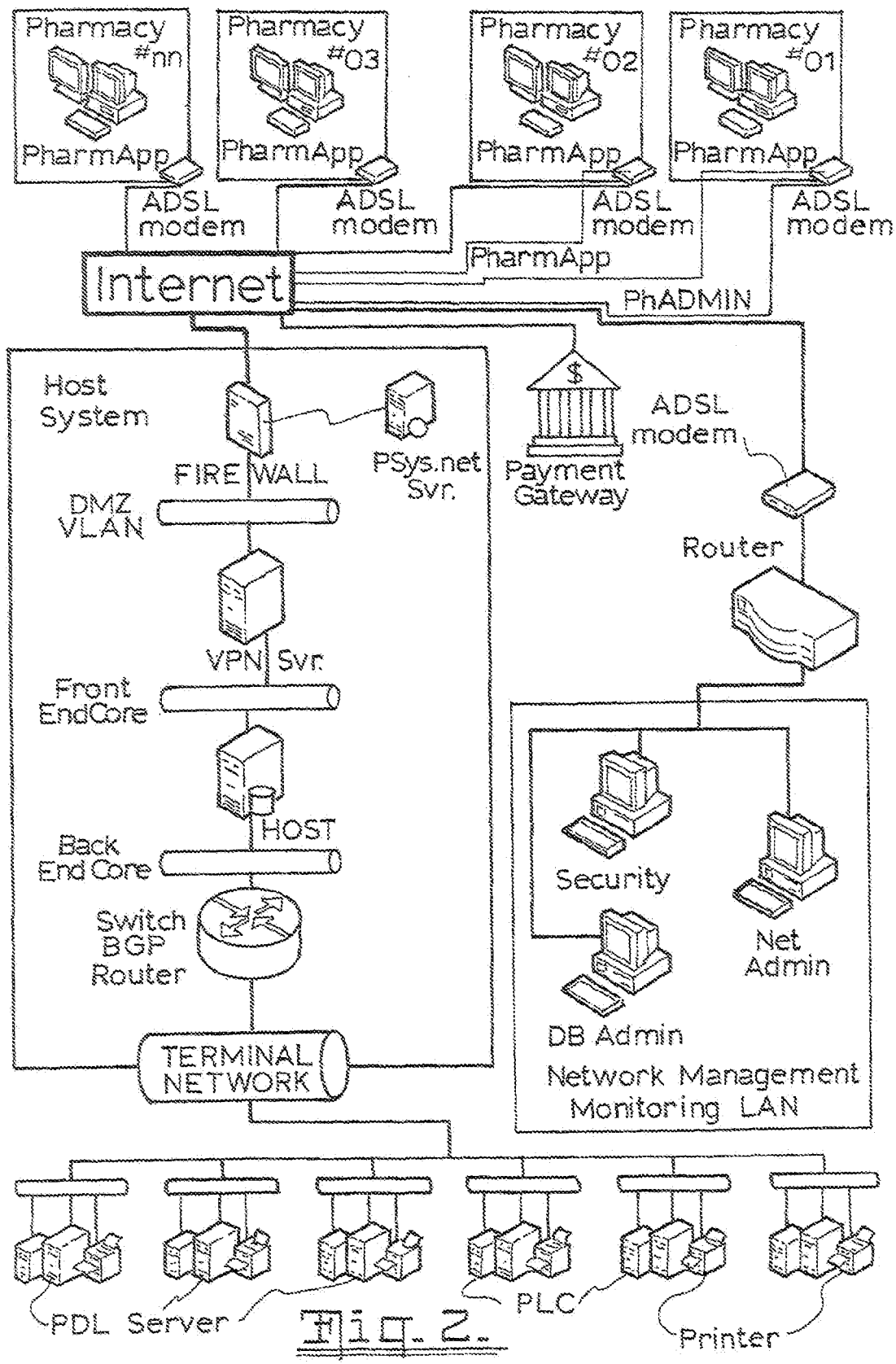
FIG. 2 is a schematic diagram of the communication network for the system of FIG. 1.
Figure 3:
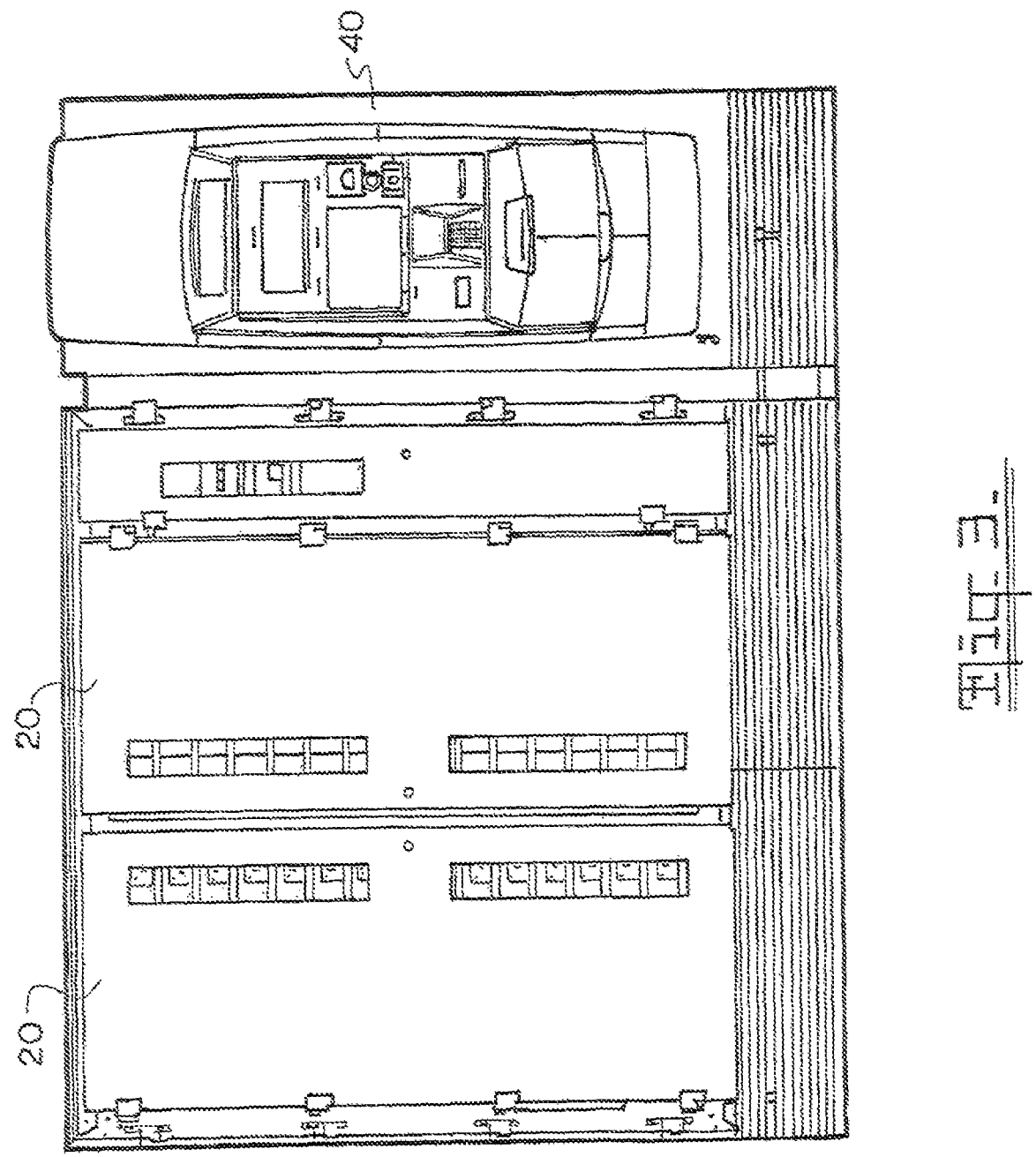
FIG. 3 is a representation of an RDM according to this embodiment.
Figure 4:
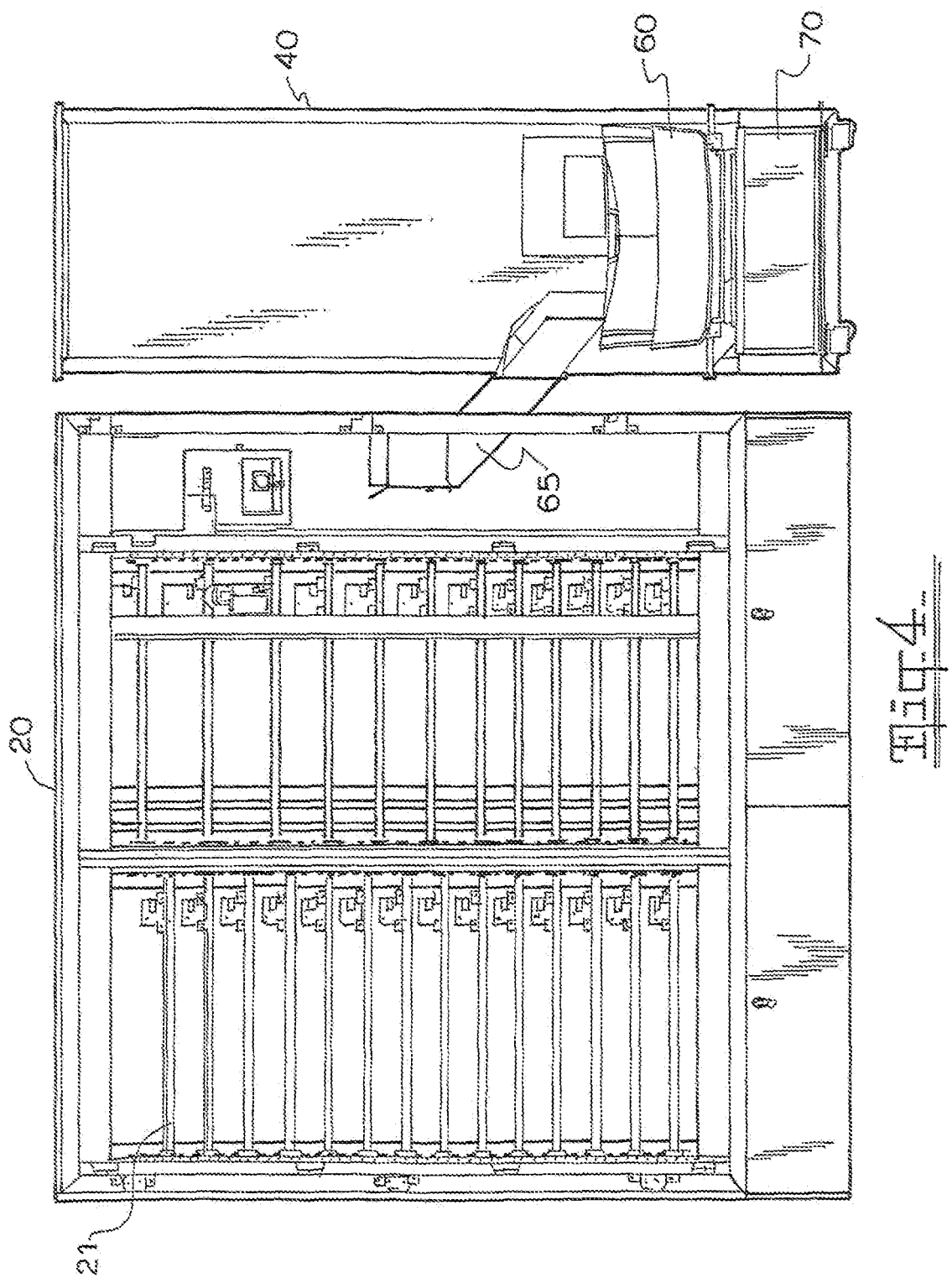
FIG. 4 is schematic front view of the inferior of the RDM of FIG. 3.

As shown in FIG. 1 the communication and control system is in three sectors namely a host to support a number of pharmacies and a number of remote dispensing machines. The host manages the queuing of RDM calls for a pharmacist and the queuing of pharmacists as they become available for consultation (see FIG. 15). The RDM incorporates arrange of devices and subsystems including a payment system generally indicated as EFTPOS. As shown in FIG. 2 each pharmacist station incorporates a computer station and keyboard and a modem for connection to host computer and its data centre. Each RDM also has an internet modem and also a bank compatible modem for the payment system. Optionally there may be access to the RDM by warehousing and retail management to monitor stocking levels and performance of the system. The remote dispensing unit as shown in FIGS. 3 to 8 comprises a sealed inventory storage unit 20 and a purchaser interface module 40. The two are linked by electronic cables and the dispensing chute 66. The storage module includes adjustable shelves 21 and which can be fixed at varying heights and spacings. The adjustable side guides 22 to form variable width compartments 23. As shown in FIG. 7 the compartments 23 may include a pressure plate 26 to urge the packs of product forward, over a low friction bass 24 to each compartment toward the forward end. The product packs are packed and stored so that the bar code is readable from the front of the storage, unit. When packed the location of each group of packs having the same bar code is stored in the RDM inventory memory. The product pickup unit moves in a space in front of the shelves 21 within the storage compartment 20. When a product is selected the pick up unit moves vertically and then horizontally to align with the compartment location as stored in the memory. The pick up unit includes a bar code reader to verify that the pack is correct. If it is net correct the pickup unit takes the packet and drops it in the reject bin chute.

Figure 9:
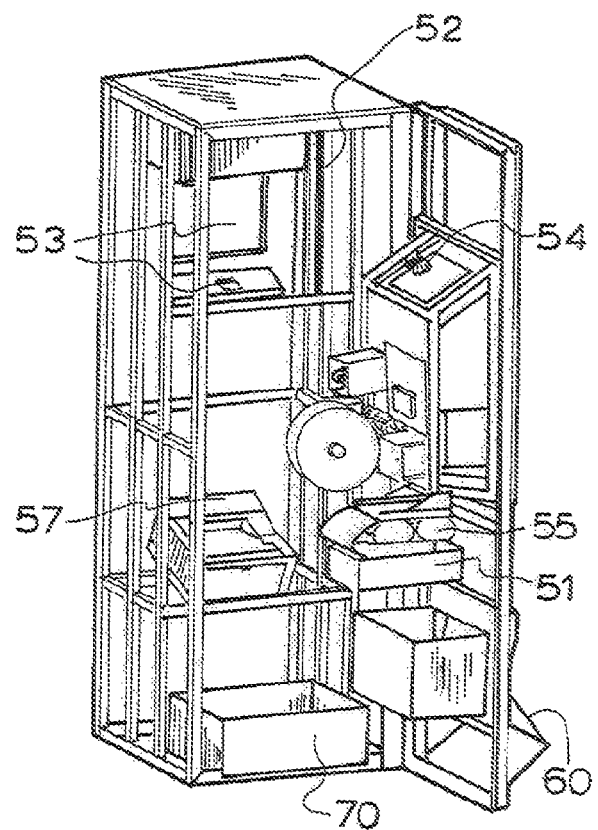
FIG. 9 is an internal view of the module of FIG. 8.
Figure 10:
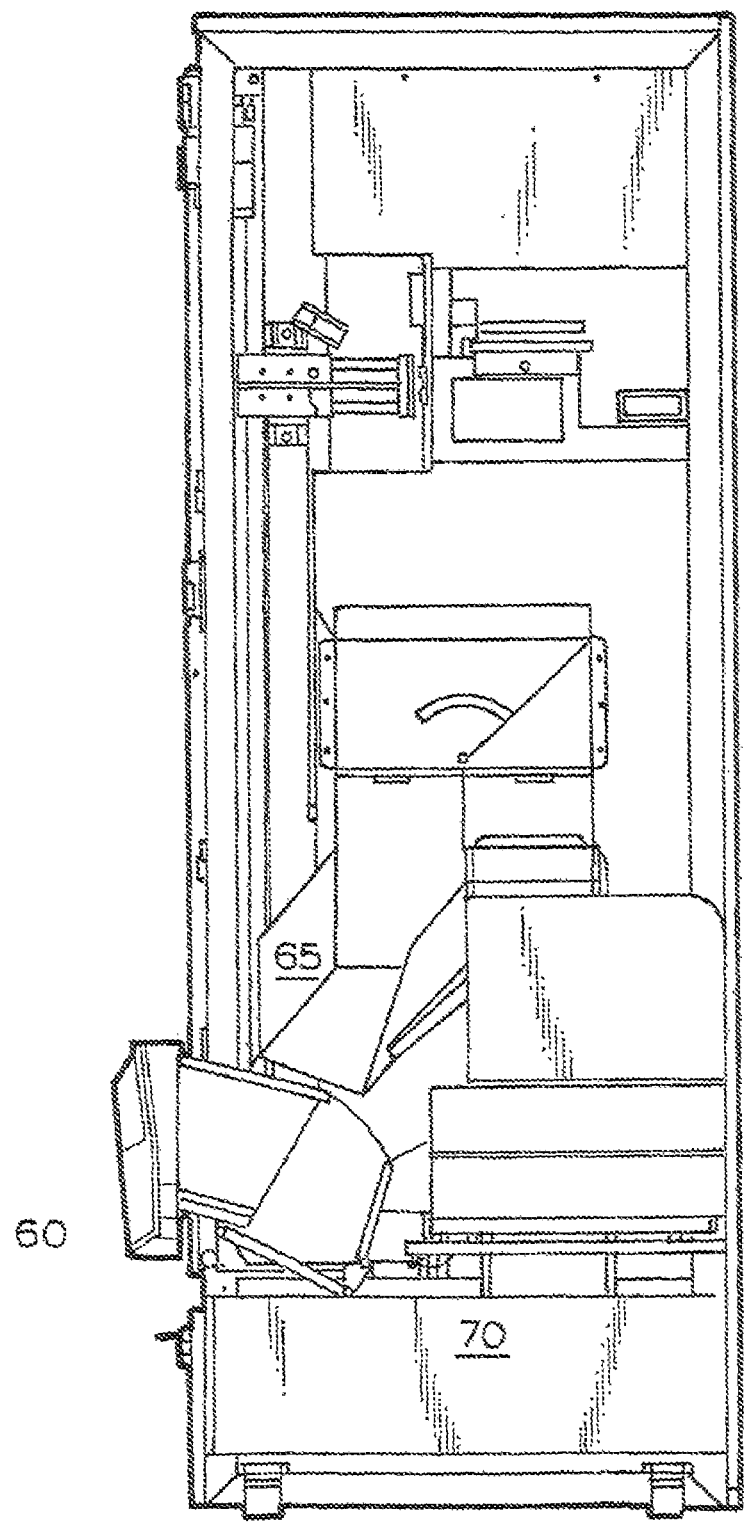
FIG. 10 is an internal end view of the module of FIG. 8.

The purchaser interface module 40 is securely bolted to the storage module 20 as shown in FIGS. 8 to 10 and includes a machine access panel 42 that is shown open in FIG. 9. The main console includes a payment panel such as a credit card or electronics fund transfer panel 43, a health card identification panel or slot 44 which may scan or photograph the card. The console may include a transaction receipt printer 46 and a repeat authorization printer 47. The RDM may be activated by actuating a transaction start key or lifting the handset 48 which connects to the available pharmacist.

The prescription scanner slot 49 allows the prescription to be processed by the script scanner 55 and then stored in the script collection drawer which has restricted access for the pharmacy staff only. A security camera 54 allows the pharmacist to view the purchaser and any identification they may need to produce, inside the module 40 is a processor and electronics mounting rack 52 and maintenance peripherals 53 as well as a label printer 57.

Figure 12B:
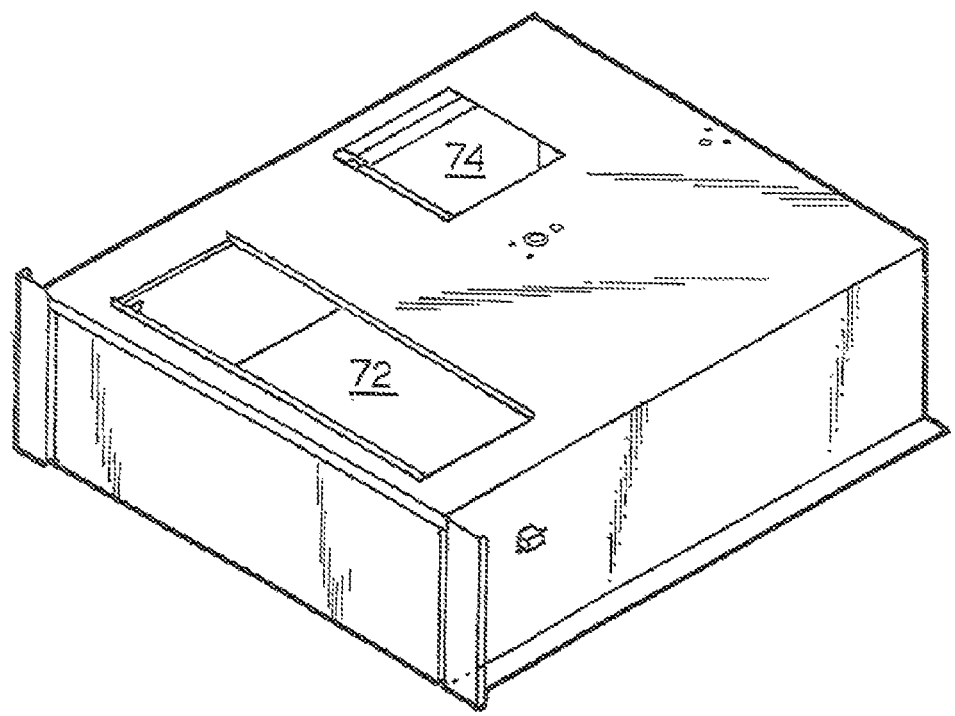
Figure 13B:
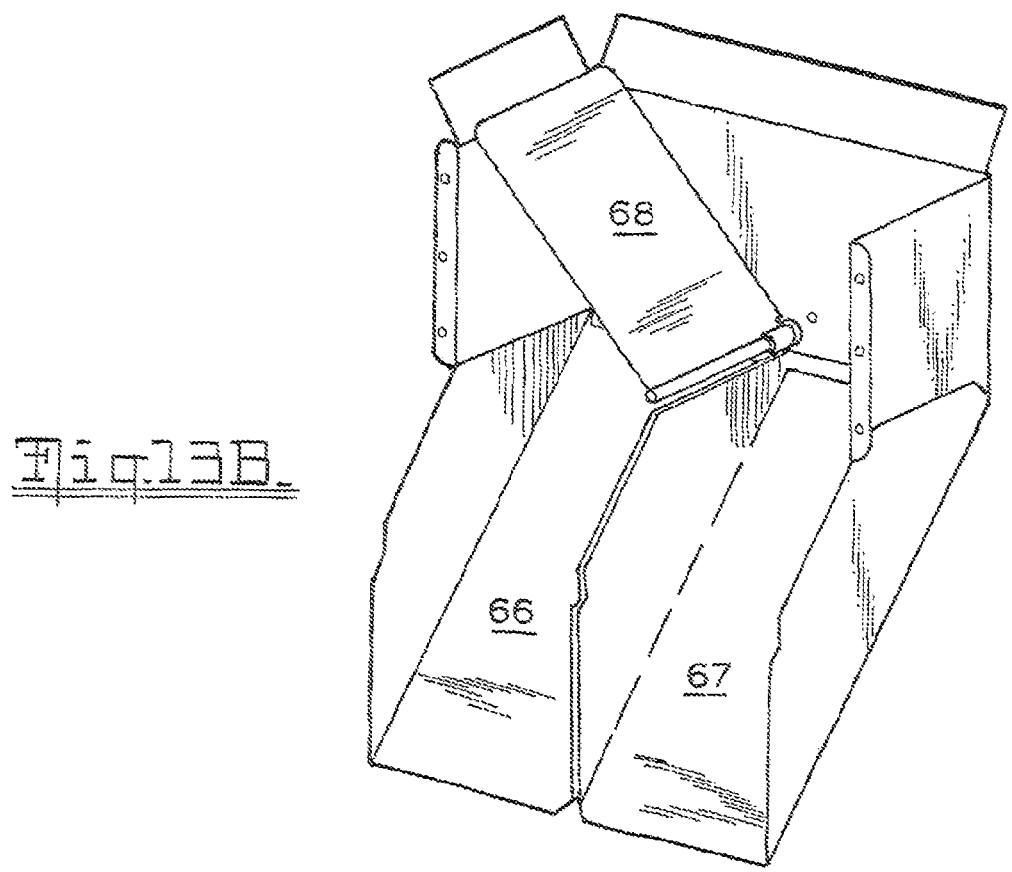

FIGS. 11A and B illustrate the issue tray, which is lockable and pivots so that when unlocked electronically by the pharmacist, it can be tilted forward to allow collection of the dispensed products. The base of the issue tray incorporates a pair of pivoted panels 62 that can be opened by movement of the lever 63, if the transaction is to be aborted after product has been deposited in the issue tray 60. The reject bin 70 shown in FIG. 12 is located below the issue tray and has opening 72 for access from the collection tray 60 and opening 74 which receives rejected product from chute 65, which is shown in detail in FIG. 13. The chute 65 has two channels 68 and 67 which may be covered by deflector plate 68. Channel 66 leads to the issue tray and channel 67 leads to opening 74 in reject bin 70. When product is verified for sending to the issue tray the deflector 68 is positioned over channel 67 before the pick up unit releases the product, if the product is to be rejected the deflector 68 is switched to cover the channel 66 so that when released from the pick up unit the product slides into the bin 70. In an alternate arrangement two reject bins are used. The second bin is preferably located in the storage unit 20 below the chute 65 so that for transactions or parts of transactions aborted prior to the product being sent to the collection tray the documents and product can go straight to the rejection bin. In this second alternative two chutes replace chute 65 and deflector plate 68. One leads to the second reject bin and the other to collection tray 60. The reject bin 70 below the collection tray 60 is then reserved for transactions aborted after the product and documentation are sent to the collection tray.

FIG. 14 illustrates the hardware components used in the RDM.

The purchaser initiates a transaction by actuating call button 100 and may also be provided with an LCD panel 101 which can display transaction instructions and if desired, provide visual images of the pharmacist. The access keypad 102 and the telephoned 48 (or a microphone and speaker unit) provide for clear communication to the pharmacist. The EFT-POS unit will include a card reader 43A and a keypad 43B.

As can be seen a number of printers are required and up to 4 video cameras are provided for the pharmacist to view the product 44A, the purchasers health card 44B and two cameras 54 to view the customer from different orientations.

The processing of a purchase is shown in FIGS. 15 and 16. Queuing programs connect an available pharmacist to the next in queue RDM. The host computer communicates with a pharmacy support software system that is used in each pharmacy. This is done through a host administration system that includes modules for billing, data storage, certification management, and auditing. The host computer also communicates with the RDM terminal and each pharmacy and provides the data and video links between the pharmacy and the RDM terminal. The voice link is preferably direct between pharmacy and the RDM terminal but an alternative is to have the voice link communicate via the host computer.

The pharmacist logs into system when available in the dispensary. The system switches the dispensing terminal to available mode, activating the terminal call button and changing information screens to advise that a pharmacist is available. The system then waits for the customer to activate the call button.

The pharmacist can fog out when leaving the dispensary. The system switches the terminal to unavailable mode, deactivating the terminal call button and changing the information screens to notify customers at the terminal that a pharmacist is not available.

The detail of the script handling is shown in FIG. 16 where the prescription is inserted in a secure script tray after which the script is scanned and the image viewed by the pharmacist.

The customer presses call button, the system notifies the pharmacist in the dispensary and the pharmacist accepts the call request. The customer is provided a call receipt which provides transaction number and relevant pharmacist contact support information.

Pharmacist welcomes customer and consults with customer as to the nature of the service. At the request of the pharmacist, the script scan lid is unlocked, customer then inserts scripts which are scanned and viewed by pharmacist in dispensary. The pharmacist can also view and/or store images of identification cards such as Medicare, Drivers Licence and health insurance cards.

In the case of an electronic prescription the customer inserts script coupon (eScript), and the system scans the coupon, reads unique ID number or bar code and notifies the eScript provider of the request. The eScript is sent to the authorised dispenser location by the provider or the coupon number is matched to the relevant eScript that has been provided to the dispenser by the prescribes on request of customer.

If the pharmacist is able to fill the request without prescription or with a prescription from the inventory in the RDM, the transaction proceeds and the script is passed to the script storage tray 51.

The pharmacist switches to the dispensing application system to complete a patient history review, clinical checks, and asks the customer questions as required and then prepares dispensing information label, CMI's and prescription repeats, if the script cannot be filled either by supply from the RDM or from the dispensary, the session is aborted and the script tray or collection tray is opened and the purchaser can remove the script.

Dispensing information is then completed by the terminal control, system while the pharmacist monitors the printing of documents, the picking of the product, views the picked product, authorises label printing, views printed label and authorises product to be placed in secure collection tray.

The sequence of events within the RDM terminal is set out in FIGS. 16-18. The product selected by the pharmacist is picked by the control mechanism sending the pick arm to the location (row and column) stored in memory. The scanner on the pick arm scans the barcode on the product at that location and verifies that the bar code is the correct one. The product is then picked and conveyed to the label printer where it is positioned at the print head. After each line of print is completed the pack is moved up one line for the next line of print or the print head moves one line while the pack remains in a fixed location. When all lines are printed the pick arm conveys the pack to the camera so that the pharmacist can view the pack barcode and the printed label. If the pack is approved the product is placed in the issue tray. During this process the system display indicates the stage in the process as shown in FIG. 17.

When the pharmacist is satisfied all items have been processed correctly, payment is completed by the customer via debit or credit or on pharmacy account. Then the receipt and repeat documents are printed and issued. Once payment is completed, the pharmacist authorises the collection tray to be unlocked and instructs customer to collect items. The pharmacist can check off supplied items with customer and complete counselling with the customer. The pharmacist closes the transaction, the collection tray is cleared, the system status is checked and then the system goes back into wait mode for next customer.

The pharmacist need not be involved in all aspects of the process as an assistant or pharmacy technician can carry out many of the steps until the final sign off for authorization by pharmacist.

As can be seen in FIGS. 17 and 18 there are check points at each step in the sequence which, if negative, result in the session being aborted and the product being placed in the reject bin.

From the above description it can be seen that this invention provides a unique and safe means of remote issue of restricted goods such as pharmaceuticals.

Those skilled in the art will realize that this invention can be implemented in a variety of embodiments without departing from the core teachings of this invention.

The invention claimed is:

1. A method of dispensing restricted products from an authorized vendor to an approved purchaser which includes the steps of
   a) providing a dispenser containing an inventory of restricted goods
   b) providing an audio communication link from the dispenser to the authorized vendor
   c) providing means in the dispenser to enable the vendor to verify the purchaser's status as an approved purchaser
   d) providing an inventory system that includes product storage in rows and columns and a product identification system that identifies the location of each product by its row and column
   e) providing a product selection device that verifies that the product selected is correct and holds and carries the product from its storage location to one or more of a printing location, viewing location and issue tray all located within the dispenser
   f) providing visual viewing means for the vendor to view the product before it is placed in the collection tray
   g) providing a payment transaction system in the dispenser to verify payment for the product
   h) providing a collection tray in the dispenser that is locked until the vendor actuates the lock to release the product to the purchaser
   i) the dispenser including a reject system that securely removes product to a reject hopper at any time after the product is held by the product selection device but prior to the vendor releasing the product from the collection tray.

2. A method as claimed in claim 1 which also includes the provision of printers to label the product and provide receipts and repeat authorizations.

3. A method as claimed in claim 1 which also includes a management server which includes a data base of approved vendors, authorized users, user locations, dispensing terminals so that the management server is programmed to assist communication between the user and the dispensing terminal.

4. A method as claimed in claim 1 wherein the reject hopper is in communication with the collection tray.

5. A dispenser for dispensing restricted goods by an authorized vendor to an approved purchaser which includes:
   a) a cabinet containing an inventory storage system, a purchaser transaction module, a reject system and a control system
   b) said inventory storage system includes product storage in rows and columns
   c) said purchaser transaction module including an audio communication link from the dispenser to the authorized vendor, a payment transaction system in the dispenser to verify payment for the product and a collection tray in the dispenser that is locked until the vendor releases the product to the purchaser
   d) said reject system securely removes product to a reject hopper at any time after the product is held by the product selection device but prior to the vendor releasing the product from the collection tray
   e) said control system including
      j) an identification device to enable the vendor to verify the purchaser's status as an approved purchaser
      ii) a product identification system that stores the location of each product by its row and column
      iii) a product selection device that enables verification that the product selected is correct and holds and carries the product from its storage location to one or more of a printing location, viewing location and issue tray all located within the dispenser
      iv) a reject key to enable the vendor to actuate the reject system; and
      v) a release key to unlock the collection tray.

6. A dispenser as claimed in claim 5 which includes a printer to print a label for the product and a transaction receipt.

7. A dispenser as claimed in claim 5 which includes a visual viewing means for the vendor to view the product before it is placed in the issue tray.

8. A dispenser as claimed in claim 5 wherein the reject hopper is in communication with the collection tray.

9. A method of dispensing pharmaceuticals at a location remote from the pharmacist which includes the steps of
   a) providing a dispenser containing an inventory of pharmaceutical products
   b) providing an audio communication link from the dispenser to the pharmacist
   c) providing a scanner and video camera in the dispenser to enable the pharmacist to verify the purchaser's status as an approved purchaser
   d) providing an inventory system that includes pharmaceutical product storage in rows and columns and a product identification system that identifies the location of each product by its row and column
   e) providing a product selection device that includes a bar code scanner and which holds and carries the product from its storage location to one or more of a printing location, viewing location, reject bin or issue tray all located within the dispenser
   f) providing visual viewing means for the pharmacist to view the product before it is placed in the issue tray
   g) providing a payment transaction system in the dispenser to verify payment for the product
   h) providing an issue tray in the dispenser that is locked until the pharmacist releases the product to the purchaser
   i) providing a reject system that securely removes product to a reject hopper at any time after the product is held by the product selection device but prior to the pharmacist releasing the product from the issue tray.

10. A method as claimed in claim 9 wherein the reject hopper is in communication with the issue tray.

* * * * *